US012310551B2

(12) United States Patent
Maurice

(10) Patent No.: US 12,310,551 B2
(45) Date of Patent: May 27, 2025

(54) APPARATUS FOR IMPROVED VISUALIZATION FOR ENDOSCOPIC PROCEDURES

(71) Applicant: ERBE-USA, Inc., Marietta, GA (US)

(72) Inventor: Daniel G. Maurice, Monument Beach, MA (US)

(73) Assignee: ERBE-USA, Inc., Marietta, GA (US)

( * ) Notice: Subject to any disclaimer, the term of this patent is extended or adjusted under 35 U.S.C. 154(b) by 264 days.

(21) Appl. No.: 16/796,135

(22) Filed: Feb. 20, 2020

(65) Prior Publication Data

US 2020/0187756 A1   Jun. 18, 2020

Related U.S. Application Data

(63) Continuation of application No. PCT/US2018/047977, filed on Aug. 24, 2018.
(Continued)

(51) Int. Cl.
*A61B 1/00* (2006.01)
*A61B 1/015* (2006.01)
*A61B 1/12* (2006.01)

(52) U.S. Cl.
CPC ...... *A61B 1/00068* (2013.01); *A61B 1/00091* (2013.01); *A61B 1/015* (2013.01); *A61B 1/126* (2013.01)

(58) Field of Classification Search
CPC ......... A61B 1/00068; A61B 1/00; A61B 1/12; A61B 1/00064; A61B 1/00098; A61B 1/00082; A61B 1/0137; A61B 1/00158
See application file for complete search history.

(56) References Cited

U.S. PATENT DOCUMENTS 3,903,877 A   9/1975   Terada
D239,025 S    3/1976   D'Alo
(Continued)

FOREIGN PATENT DOCUMENTS

CN    101507597 A    8/2009
EP      0082950 A2    7/1983
(Continued)

OTHER PUBLICATIONS

Extended European Search Report for European Patent Application No. 18848761.5, mailed Mar. 24, 2021, 9 pages.
(Continued)

*Primary Examiner* — Aaron B Fairchild
*Assistant Examiner* — Megan Elizabeth Monahan
(74) *Attorney, Agent, or Firm* — COOLEY LLP

(57) ABSTRACT

Embodiments described herein relate to a valve assembly for an endoscopic device and methods of using the same. The valve assembly can be disposed in a receptacle and operably coupled to a gas inlet port, a gas outlet port, a water inlet port, and a water outlet port. The valve assembly can include a valve stem defining a first channel, a second channel, a third channel, and a fourth channel fluidically coupled to an adjustable sealing member. During at least one of insufflation, irrigation, and lens cleaning, communication of gas between the gas supply and the water outlet port is prevented when gas is communicated through the fourth channel via the first channel and the third channel such that the gas exerts a sealing pressure on the adjustable sealing member.

39 Claims, 8 Drawing Sheets

Related U.S. Application Data

(60) Provisional application No. 62/549,698, filed on Aug. 24, 2017.

(56) References Cited

U.S. PATENT DOCUMENTS

| | | | |
|---|---|---|---|
| D245,921 S | 9/1977 | Beran |
| 4,253,448 A | 3/1981 | Terada |
| 4,301,799 A | 11/1981 | Pope, Jr. et al. |
| 4,311,134 A | 1/1982 | Mitsui et al. |
| 4,325,362 A | 4/1982 | Ouchi et al. |
| D266,790 S | 11/1982 | McCord |
| D271,618 S | 11/1983 | Nishigaki |
| 4,489,712 A | 12/1984 | Ohshima |
| 4,542,130 A | 9/1985 | Weissmuller et al. |
| 4,548,197 A | 10/1985 | Kinoshita |
| 4,552,130 A | 11/1985 | Kinoshita |
| 4,667,655 A | 5/1987 | Ogiu et al. |
| 4,760,838 A | 8/1988 | Fukuda |
| D300,361 S | 3/1989 | Tokarz |
| 4,828,295 A | 5/1989 | Plaquin et al. |
| 4,844,052 A | 7/1989 | Iwakoshi et al. |
| D302,729 S | 8/1989 | Stephens et al. |
| 5,027,791 A | 7/1991 | Takahashi |
| D325,023 S | 3/1992 | Lee et al. |
| 5,133,336 A | 7/1992 | Savitt et al. |
| 5,151,101 A | 9/1992 | Grossi et al. |
| 5,152,746 A | 10/1992 | Atkinson et al. |
| 5,191,878 A | 3/1993 | Lida et al. |
| D340,316 S | 10/1993 | Zdrok |
| 5,297,537 A | 3/1994 | Savitt et al. |
| 5,328,478 A | 7/1994 | McVay |
| 5,402,770 A | 4/1995 | Lida et al. |
| 5,437,654 A | 8/1995 | McVay |
| 5,470,324 A | 11/1995 | Cook et al. |
| D366,863 S | 2/1996 | Lee |
| D371,513 S | 7/1996 | Scudder et al. |
| 5,536,254 A | 7/1996 | McVay |
| 5,630,795 A | 5/1997 | Kuramoto et al. |
| 5,707,351 A | 1/1998 | Dorsey, III |
| 5,807,313 A | 9/1998 | Delk et al. |
| 5,830,128 A | 11/1998 | Tanaka |
| 6,027,499 A | 2/2000 | Johnston et al. |
| D435,513 S | 12/2000 | Cheng |
| 6,210,322 B1 | 4/2001 | Byrne |
| 6,287,848 B1 | 9/2001 | Hamzeh et al. |
| 6,485,412 B1 | 11/2002 | Byrne |
| 6,499,615 B1 | 12/2002 | Szieff et al. |
| 6,523,711 B1 | 2/2003 | Hughes et al. |
| D472,630 S | 4/2003 | Douglas et al. |
| 6,764,442 B2 | 7/2004 | Ota et al. |
| D496,998 S | 10/2004 | Pajunk et al. |
| 6,855,109 B2 | 2/2005 | Obata et al. |
| D530,669 S | 10/2006 | Shing |
| 7,204,382 B2 | 4/2007 | Cezeaux |
| D543,509 S | 5/2007 | Victor |
| 7,276,023 B2 | 10/2007 | Annecke |
| 7,462,068 B2 | 12/2008 | Amidon |
| D612,496 S | 3/2010 | Bennison |
| 7,678,044 B2 | 3/2010 | Fujikura |
| D613,403 S | 4/2010 | Poll et al. |
| D624,181 S | 9/2010 | Harata et al. |
| D627,039 S | 11/2010 | Yu |
| D636,079 S | 4/2011 | Leypold et al. |
| D652,923 S | 1/2012 | Kennedy et al. |
| D657,870 S | 4/2012 | Becker |
| 8,152,790 B2 | 4/2012 | Lopez et al. |
| D661,257 S | 6/2012 | Natoli |
| 8,206,375 B2 | 6/2012 | Snow |
| 8,231,574 B2 | 7/2012 | Haack et al. |
| 8,308,726 B2 | 11/2012 | Kumar et al. |
| 8,333,690 B2 | 12/2012 | Ikeda |
| D676,544 S | 2/2013 | Blocher |
| D678,521 S | 3/2013 | Mort et al. |
| 8,435,172 B2 | 5/2013 | Banik et al. |
| 8,485,818 B2 | 7/2013 | Boutoussov et al. |
| 8,535,219 B2 | 9/2013 | Smith et al. |
| D693,465 S | 11/2013 | Koehler et al. |
| 8,764,642 B2 | 7/2014 | Bendele et al. |
| D712,014 S | 8/2014 | Guest |
| 8,870,756 B2 | 10/2014 | Maurice |
| D717,432 S | 11/2014 | Leroy et al. |
| D719,650 S | 12/2014 | Arinobe et al. |
| D724,703 S | 3/2015 | Downs |
| D732,664 S | 6/2015 | Woehr et al. |
| D739,527 S | 9/2015 | Chauvette |
| 9,144,374 B2 | 9/2015 | Maurice |
| D741,805 S | 10/2015 | Davidson, Jr. |
| D742,508 S | 11/2015 | Row et al. |
| D749,212 S | 2/2016 | Chauvette |
| D749,213 S | 2/2016 | Chauvette |
| D750,235 S | 2/2016 | Maurice |
| D750,236 S | 2/2016 | Maurice |
| 9,307,890 B2 | 4/2016 | Ouchi |
| 9,408,523 B2 | 8/2016 | Grudo et al. |
| D777,112 S | 1/2017 | Watkins |
| D785,790 S | 5/2017 | Lewis et al. |
| D791,310 S | 7/2017 | Maurice |
| D791,939 S | 7/2017 | Turturro et al. |
| D791,940 S | 7/2017 | Maurice |
| D793,551 S | 8/2017 | Nelson |
| D796,035 S | 8/2017 | Turturro et al. |
| D797,927 S | 9/2017 | Schuessler et al. |
| D799,031 S | 10/2017 | Barrett et al. |
| D805,637 S | 12/2017 | Bureau |
| D816,211 S | 4/2018 | Guala |
| D820,980 S | 6/2018 | Maurice |
| D825,737 S | 8/2018 | Yokoyama |
| D826,400 S | 8/2018 | Nelson |
| D827,130 S | 8/2018 | Penttila |
| 10,052,472 B2 | 8/2018 | Maurice |
| D831,201 S | 10/2018 | Holtz et al. |
| 10,098,525 B2 | 10/2018 | Maurice |
| 10,111,578 B2 | 10/2018 | Maurice |
| D835,266 S | 12/2018 | Maurice |
| D848,602 S | 5/2019 | Yokoyama |
| D867,587 S | 11/2019 | Holtz et al. |
| D867,588 S | 11/2019 | Rogge et al. |
| D867,913 S | 11/2019 | Hietala et al. |
| D912,246 S | 3/2021 | Maurice |
| 10,952,595 B2 | 3/2021 | Maurice |
| 11,406,251 B2 | 8/2022 | Maurice |
| 2001/0039370 A1 | 11/2001 | Takahashi et al. |
| 2002/0040181 A1 | 4/2002 | Arai et al. |
| 2002/0092858 A1 | 7/2002 | Bowman |
| 2002/0185379 A1 | 12/2002 | Schrenk et al. |
| 2003/0018238 A1 | 1/2003 | Obata et al. |
| 2003/0045779 A1 | 3/2003 | Ito |
| 2005/0025646 A1 | 2/2005 | Miller et al. |
| 2005/0159702 A1 | 7/2005 | Sekiguchi et al. |
| 2005/0215856 A1 | 9/2005 | Fujikura |
| 2005/0222499 A1 | 10/2005 | Banik et al. |
| 2005/0263480 A1 | 12/2005 | Smolko et al. |
| 2006/0047184 A1 | 3/2006 | Banik et al. |
| 2006/0052665 A1 | 3/2006 | Aizenfeld et al. |
| 2006/0052666 A1 | 3/2006 | Kumar et al. |
| 2006/0229498 A1 | 10/2006 | Kohno |
| 2006/0241348 A1 | 10/2006 | Kohno |
| 2006/0252989 A1 | 11/2006 | Bar-Or et al. |
| 2006/0266423 A1 | 11/2006 | Akiba et al. |
| 2007/0043262 A1 | 2/2007 | Levy et al. |
| 2007/0161970 A1 | 7/2007 | Spohn et al. |
| 2007/0204890 A1 | 9/2007 | Torii |
| 2007/0225566 A1 | 9/2007 | Kawanishi |
| 2007/0238929 A1 | 10/2007 | Aizenfeld et al. |
| 2007/0244363 A1 | 10/2007 | Sano et al. |
| 2007/0255256 A1 | 11/2007 | Fischer et al. |
| 2008/0091061 A1 | 4/2008 | Kumar et al. |
| 2008/0125629 A1 | 5/2008 | Banik et al. |
| 2008/0154095 A1 | 6/2008 | Stubkjaer et al. |
| 2008/0167527 A1 | 7/2008 | Slenker et al. |
| 2008/0193631 A1 | 8/2008 | Kanamori et al. |
| 2008/0214891 A1 | 9/2008 | Slenker et al. |
| 2009/0023996 A1 | 1/2009 | Fujikura |
| 2009/0032533 A1 | 2/2009 | Kessell et al. |

(56) References Cited

U.S. PATENT DOCUMENTS

| | | |
|---|---|---|
| 2009/0090398 A1 | 4/2009 | Onishi |
| 2009/0209822 A1 | 8/2009 | Ikeda |
| 2009/0264705 A1 | 10/2009 | Cushner et al. |
| 2009/0306476 A1 | 12/2009 | Banik et al. |
| 2010/0010307 A1 | 1/2010 | Schramm |
| 2010/0094089 A1 | 4/2010 | Litscher et al. |
| 2010/0125164 A1 | 5/2010 | LaBombard |
| 2010/0185139 A1 | 7/2010 | Stearns et al. |
| 2010/0210907 A2 | 8/2010 | Schramm |
| 2010/0256448 A1 | 10/2010 | Smith et al. |
| 2010/0292644 A1 | 11/2010 | Haack et al. |
| 2011/0004065 A2 | 1/2011 | Schramm |
| 2011/0263939 A1 | 10/2011 | Kaye et al. |
| 2012/0088973 A1 | 4/2012 | Morimoto |
| 2012/0088974 A1 | 4/2012 | Maurice |
| 2012/0091092 A1 | 4/2012 | Adams et al. |
| 2012/0095293 A1 | 4/2012 | Bendele et al. |
| 2012/0095391 A1 | 4/2012 | Bendele et al. |
| 2012/0095537 A1 | 4/2012 | Hall et al. |
| 2014/0309496 A1 | 10/2014 | Bendele et al. |
| 2014/0316205 A1 | 10/2014 | Bendele et al. |
| 2015/0141757 A1 | 5/2015 | Maurice |
| 2015/0257634 A1* | 9/2015 | Nakade .................. A61B 1/005 29/890.12 |
| 2015/0374213 A1 | 12/2015 | Maurice |
| 2016/0089002 A1 | 3/2016 | Burton et al. |
| 2016/0121095 A1 | 5/2016 | Maurice |
| 2017/0265727 A1 | 9/2017 | Maurice |
| 2019/0223701 A1 | 7/2019 | Maurice |
| 2020/0121171 A1 | 4/2020 | Kaye et al. |
| 2023/0210352 A1 | 7/2023 | Maurice |

FOREIGN PATENT DOCUMENTS

| | | |
|---|---|---|
| JP | S59151930 A | 8/1984 |
| JP | S62-277935 A | 12/1987 |
| JP | H0373101 U | 7/1991 |
| JP | 07-053149 | 6/1995 |
| JP | 08-106052 | 4/1996 |
| JP | H109398 A | 1/1998 |
| JP | 2003093334 A | 4/2003 |
| JP | 2003305003 A | 10/2003 |
| JP | 2004202248 A | 7/2004 |
| JP | 2004-242877 A | 9/2004 |
| JP | 2009-504302 | 2/2009 |
| JP | 2013085755 A | 5/2013 |
| JP | 2017509436 A | 4/2017 |
| RU | 2372040 C2 | 11/2009 |

OTHER PUBLICATIONS

Extended European Search Report for European Patent Application No. 11008045.4, dated Jun. 19, 2012, 7 pages.

Gima, Adapter Wolf Endoscope, Product Description [online], Retrieved from the Internet: <https://www.gimaitaly.com/prodotti.asp?sku=30845&dept_selected=470&dept_id=4701, Retrieved on May 7, 2020, 1 page.

International Search Report and Written Opinion for International Application No. PCT/US2018/047977, mailed Oct. 26, 2018, 10 pages.

Office Action for U.S. Appl. No. 13/230,576, mailed Aug. 2, 2013, 12 pages.

Office Action for U.S. Appl. No. 13/230,576, mailed Feb. 25, 2014, 25 pages.

Office Action for U.S. Appl. No. 14/496,309, mailed Apr. 1, 2015, 27 pages.

Office Action for U.S. Appl. No. 14/529,967, mailed Jul. 18, 2017, 7 pages.

Final Office Action for U.S. Appl. No. 14/529,967, mailed Dec. 26, 2017, 9 pages.

Office Action for U.S. Appl. No. 14/832,567, mailed Jan. 2, 2018, 12 pages.

Office Action for U.S. Appl. No. 15/610,501, mailed Jan. 4, 2018, 13 pages.

Ex-Parte Quayle Action in U.S. Appl. No. 29/605,341, mailed Feb. 7, 2018, 6 pages.

Office Action for U.S. Appl. No. 16/130,440, mailed May 12, 2020, 11 pages.

Office Action for U.S. Appl. No. 29/667,080, mailed May 12, 2020, 6 pages.

Office Action for U.S. Appl. No. 17/401,264, mailed Dec. 9, 2021, 6 pages.

First Office Action for Chinese Application No. 201880064429.3, issued Apr. 6, 2022, 19 pages.

First Office Action for Indian Application No. 202017008204, dated Feb. 25, 2022, 6 pages.

Notice of Reasons for Rejection for Japanese Application No. 2020-511483, mailed Jun. 28, 2022, 12 pages.

Office Action for Russian Application No. 2020111231/14(018884), dated Jan. 26, 2022, 14 pages.

Notice of Hearing in IN Application No. 202017008204, mailed Mar. 21, 2024, 3 pages.

* cited by examiner

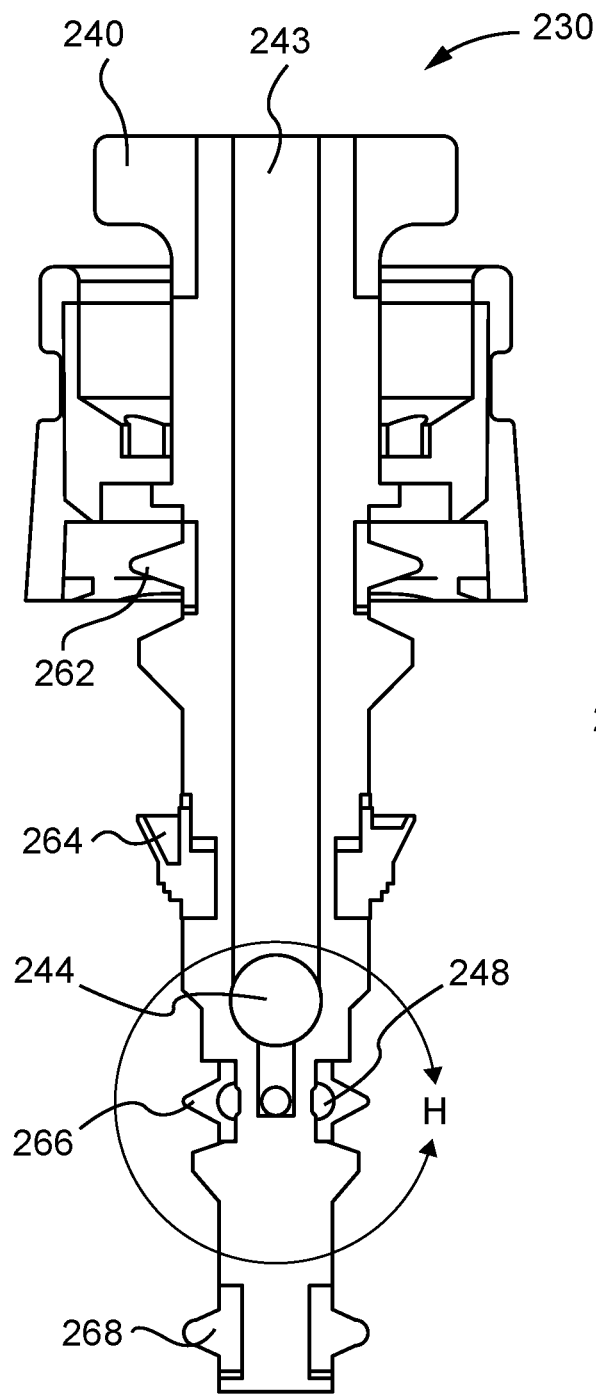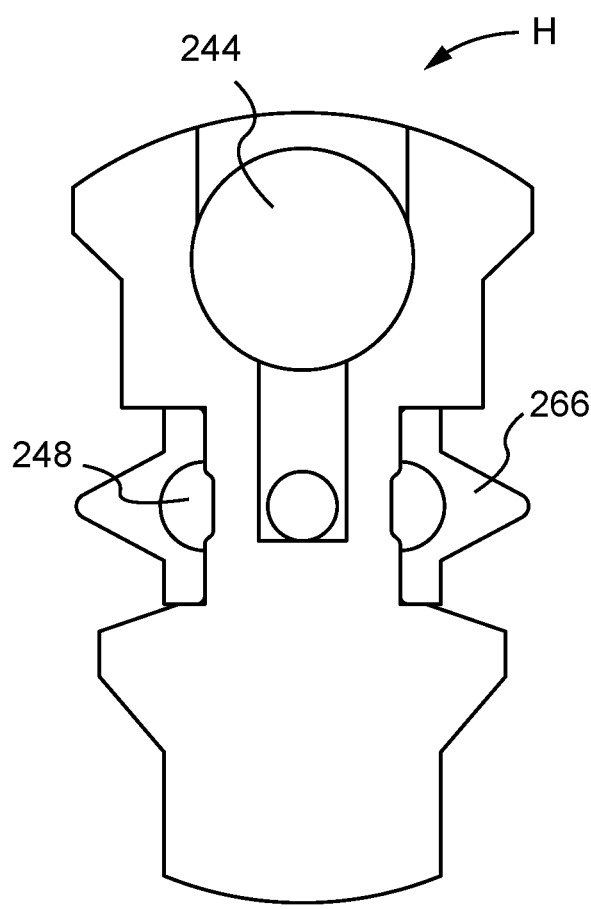

APPARATUS FOR IMPROVED VISUALIZATION FOR ENDOSCOPIC PROCEDURES

CROSS-REFERENCE TO RELATED APPLICATIONS

This application is a continuation of International Patent Application No. PCT/US2018/047977, filed Aug. 24, 2018, titled "Apparatus for Improved Visualization for Endoscopic Procedures," which claims priority to, and the benefit of U.S. Provisional Application No. 62/549,698 filed on Aug. 24, 2017, titled "Apparatus for Improved Visualization for Endoscopic Procedures," the contents of which are incorporated herein by reference in their entirety.

BACKGROUND

Endoscopic systems are configured to aid in internal visualization and facilitate clinical activities (i.e., surgery, biopsies, visual inspection, etc.). Endoscopic systems often include a handle, an articulated probe, and a gas/water valve configured to select between insufflation and/or water. Some commercially available endoscopic systems experience diminished visualization during insufflation due at least in part to an unintended bypass of water past a gasket in the gas/water valve that subsequently leaks across a lens positioned in a distal portion of the articulated probe.

SUMMARY

Embodiments described herein relate to an apparatus including an endoscope handle configured to be coupled to a gas supply system and a water supply system, the endoscope handle defining a receptacle including a gas inlet port, a gas outlet port, a water inlet port, and a water outlet port. A gas/water valve including a vent is disposed in the receptacle and defines a first fluid flow path, a second fluid flow path, and a third fluid flow path. The gas/water valve is configured to be transitioned between a first configuration in which the gas inlet port is placed in fluid communication with the vent such that gas can flow from the gas supply system, through the first fluid flow path and out the vent, a second configuration in which the gas inlet port is placed in fluid communication with the gas outlet port such that gas can flow from the gas supply system, through the second fluid flow path and out the gas outlet port, and a third configuration in which the water inlet port is placed in fluid communication with the water outlet port such that water can flow from the water supply system, through the third fluid flow path and out the water outlet port.

In some embodiments, the gas/water valve includes a sealing member configured to be disposed between the gas inlet port and the gas outlet port. In some embodiments, the sealing member is configured to be deformed to establish the second fluid flow path in the second configuration. In some embodiments, the sealing member is a first sealing member and the gas/water valve includes a second sealing member configured to be disposed between the gas/water inlet ports and gas/water outlet ports in the first configuration and the second configuration. In some embodiments, the apparatus further includes an actuator operably coupled to the gas/water valve and configured to move the second sealing member from a first position to a second position when actuated by a user to establish the third fluid flow path in the third configuration.

BRIEF DESCRIPTION OF THE DRAWINGS

FIG. 4 is a cross-sectional view of a gas/water valve, according to an embodiment.

FIG. 5 is an enlarged cross-sectional view of the portion of FIG. 4 identified by the circle H.

DETAILED DESCRIPTION

Figure 1:
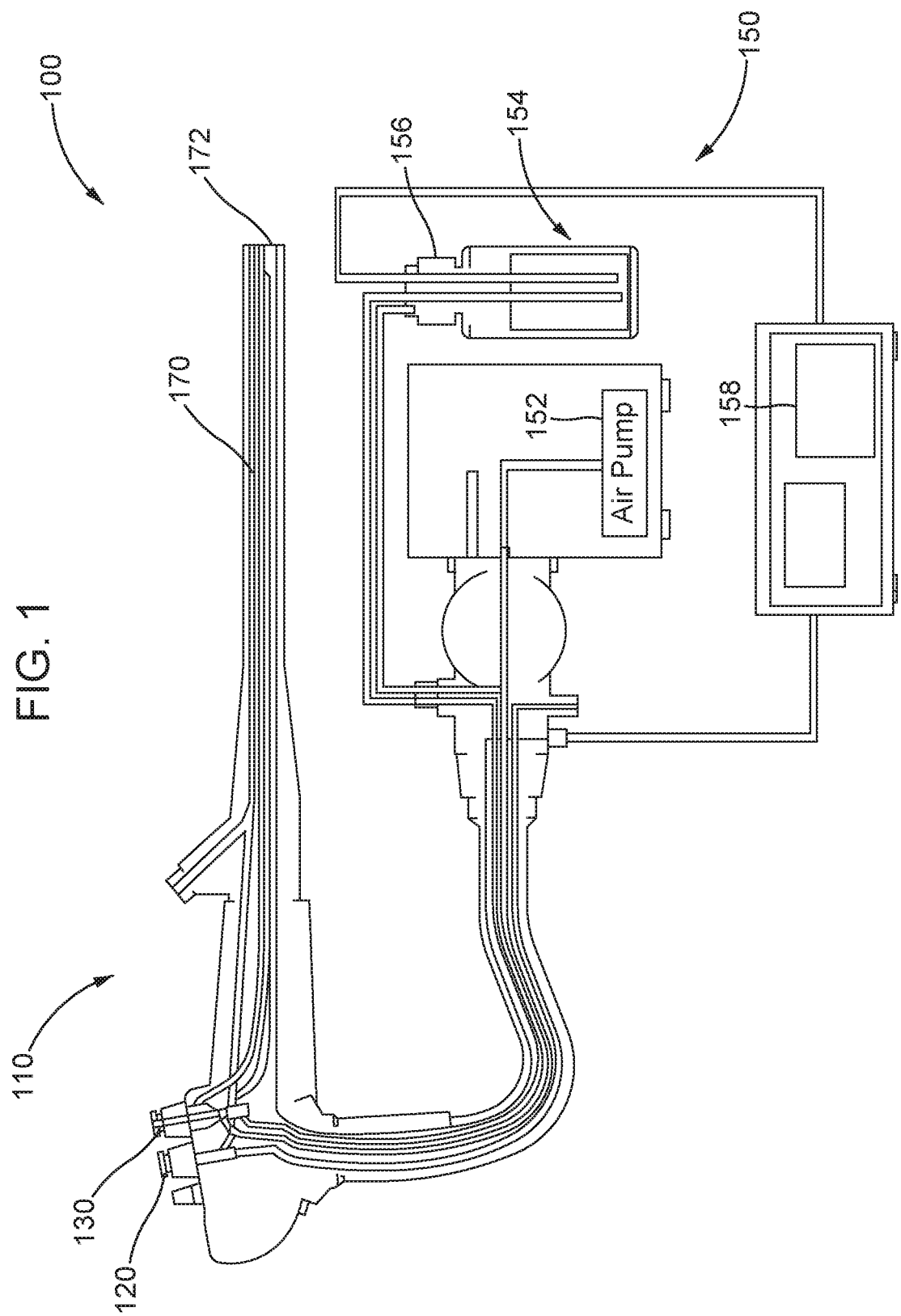
FIG. 1 is a schematic illustration of an endoscope system, according to an embodiment.

Embodiments described herein relate to an apparatus including an endoscope handle configured to be coupled to a gas supply (e.g., a supply of air, $CO_2$, or any other suitable gas) and a water supply, the endoscope handle defining a receptacle including a gas inlet port, a gas outlet port, a water inlet port, and a water outlet port. A gas/water valve including a vent is disposed in the receptacle and defines a first fluid flow path, a second fluid flow path, and a third fluid flow path. The gas/water valve is configured to be transitioned between a first configuration in which the gas inlet port is placed in fluid communication with the vent such that gas can flow from the gas supply, through the first fluid flow path and out the vent, a second configuration in which the gas inlet port is placed in fluid communication with the gas outlet port such that gas can flow from the gas supply, through the second fluid flow path and out the gas outlet port, and a third configuration in which the water inlet port is placed in fluid communication with the water outlet port such that water can flow from the water supply, through the third fluid flow path and out the water outlet port. In some embodiments, an adjustable sealing member is disposed about the valve stem and is configured to expand to prevent communication of gas between the gas supply system and the water supply system when the gas/water valve is in the second configuration.

The desire to visualize inside the "living" human body via a light guiding tube instrument dates back to the early 1800's. The following several decades yielded advancements in light guiding tube instruments with the first successful visualization of the inside of a living human stomach toward the end of the century, followed by continued advancements with flexible fiberscopes in the early 1960's. Today, many structures once considered beyond the realm of diagnostic evaluation and therapeutic intervention can now be visualized and treated by an endoscopist. For example, without the use of an "open" surgical technique, an endoscopist can provide a diagnostic evaluation and therapeutic intervention of several different areas within the gastrointestinal tract. The diagnosis and treatment of many gastrointestinal (GI) disorders such as foreign body removal, gallstone removal, polyp removal, tissue biopsy, structure dilatation, stent placement (for patency and drainage), bleeding and hemostasis, requires constant visualization and inspection in order to assess the inner parts of the gastrointestinal tract. As newly developed advanced procedures (POEM, Endoscopic Gastric Sleeve, ESD, etc.) become more commonplace, physicians' requirements for improvements in visualization also need to be addressed.

Due to the lower morbidity and mortality associated with endoscopic procedures and the increased utility associated with "higher" risk patient populations, endoscopic diagnostic and therapeutic interventions are the most widely performed medical procedures in the United States. There are three primary endoscope manufacturers who share approximately 80%, 15%, and 5% of the US Market, Olympus, Pentax, and Fujinon, respectively. Each of the systems are utilized in a similar fashion, however, the operations and internal features of the manufacturers endoscopes vary. In 2009, 55 million procedures were performed using GI endoscopic devices. Approximately 50 percent of the procedures performed were colonoscopies (28 million).

As described herein, endoscopic devices can be used for any endoscopic procedures, including but not limited to esophagogastroduodenoscopies, colonoscopies, sigmoidoscopy, endoscopic retrograde cholangiopancreatography, rhinoscopy, bronchoscopy, cystoscopy, gynoscopy, colposcopy, hysteroscopy, falloposcopy, laparoscopy, thoracoscopy, enteroscopy, amnioscopy, fetoscopy, panendoscopy, epiduroscopy, and any combinations thereof. Endoscopic devices can be connected to a water source, a gas source, an electrical source, a vacuum source, and/or a light source to facilitate visualization of the internal organ or object and/or to facilitate movement of the endoscope/probe through the body.

An endoscopic system as described herein includes an endoscope handle configured to be coupled to a control unit, and a flexible shaft extending from the endoscope handle and terminating in a distal end that can be articulated by a user. In other words, the user can control the movement of the distal end of the flexible shaft along with the various functions of the endoscopic system with the endoscope handle. The endoscopic system can be used to visualize inside the living organism and to facilitate other medical procedures when necessary. The control unit includes a gas supply system, a water supply system, an electrical source, a vacuum source, a light source, and/or other ancillary systems and apparatuses. The flexible shaft is typically inserted into a body cavity such as the mouth, vagina, anus, urethra, a small incision, or other such cavity to facilitate visualization of an internal organ or object without necessitating an invasive surgical procedure. The distal end of the flexible shaft includes a lens connected to a video camera such that a real-time image of the interior space can be captured and viewed during the procedure. The endoscopic system can be similar to that described in U.S. Pat. Nos. 8,870,756 and 9,144,374, the disclosures of which are hereby incorporated herein in their entireties.

During a routine diagnostic colonoscopy or a more complicated treatment of acute lower gastrointestinal bleeding, it is not uncommon to encounter mucus secretions, stool, and or bleeding which limits the endoscopist's visualization and therapeutic capabilities. To maintain a clear operative field and also acceptable visualization, a typical endoscopic system includes a sub-system for opening or insufflating the gastrointestinal tract with a gas, a sub-system for delivering sterile water for endoscopic irrigation (i.e., lavage), and a sub-system for delivering a liquid (e.g., sterile water) for optical lens cleaning. The two primary functions that are used during an endoscopic procedure are suction and gas/water delivery. These operations are manually controlled by a physician who initiates the associated function with controls (e.g., valves) on the endoscope handle. A first valve (e.g., a suction valve) is primarily used to remove gas, fluid, or debris from the GI tract; however, it can also be used to facilitate the manipulation of a tissue position prior to resection or other intervention. A second valve (e.g., a gas/water valve) is primarily used to insufflate lumens within the GI tract and provide fluid for lens cleaning. In order to distend the lumen when using an endoscopic system, gas is delivered from the console via the endoscope by covering the gas release hole (also referred to herein as a "vent") on the gas/water valve, however, when doing so, water is typically and also unintentionally forced out of the lens rinsing water line causing "blurred" vision for a period of time while insufflating. Depending on the procedure, this inadvertent release of fluid could have serious unintended consequences resulting in patient injury.

As described herein, each of the endoscope systems are utilized in a similar fashion, however, the operations and internal features of the manufacturers' endoscopes can vary. In a standard endoscope (colonoscope or gastroscope), both the gas/water and suction valves are inserted into their respective receiving receptacles (also referred to herein as "cylinders" or "receiving cylinders") in the endoscope handle. The receptacles are typically machined out of a durable material (e.g., stainless steel) and generally follow the outer contours of the specific valve with an extremely small engineering tolerance and also allow for inputs and outputs based on the respective valve functions. Specifically, as it relates to the operation of the gas/water valve, the receiving cylinder allows for two inputs, which enter at the proximal portion of the endoscope umbilical, gas in and water in, and also has two outputs, which exit the receiving cylinder toward the distal end of the endoscope, gas out and water out. In addition, the gas/water valve has several different seals on the valve stem and three functional configurations when disposed in the receiving cylinder (i.e., open, covered, and depressed).

In some embodiments, when the gas/water valve is in use, the open configuration allows gas to pass from the control unit, through the gas inlet port and into a central location within the receiving cylinder between two seals on the valve stem, and exit the endoscope to ambient through the gas release hole (also known as "vent") in the center of the gas/water valve. When the gas/water valve vent is digitally covered by the physician, the receiving cylinder begins to pressurize, and a first seal on the valve stem intentionally begins to deform, which allows the gas to be redirected past the seal and to exit the receiving cylinder via the gas outlet port to the distal end of the flexible shaft. When the gas/water valve is depressed, the gas can no longer enter the receiving cylinder and it is redirected to the water supply system, which begins to pressurize and force fluid (e.g., sterile water) to flow from the water supply system, through the endoscope umbilical to the water inlet port, through the receiving cylinder (e.g., about the valve stem between two seals) to the water outlet port, and to the distal end of the flexible endoscope. In practice, when the gas/water valve airflow release hole is digitally covered by the physician and the receiving cylinder begins to pressurize, a second seal on the valve stem begins to unintentionally deform, which allows the gas to leak past the second seal and exit the receiving cylinder via the water outlet port resulting in an inadvertent release of fluid and "blurred" vision. Since insufflation is regularly used throughout many endoscopic procedures, a user often continues with insufflation despite diminished visual clarity. Therefore, there is a need for a gas/water valve that does not leak water across the lens during insufflation.

In some embodiments, such an apparatus can include a valve assembly configured to be disposed in a receptacle of an endoscope handle, the receptacle including a gas inlet port, a gas outlet port, a water inlet port, and a water outlet port, and configured to be in fluidic communication with a gas supply system and a water supply system. In some embodiments, the valve assembly can include a valve stem including a valve inlet port, a valve outlet port, and a vent. In some embodiments, the apparatus can include an adjustable sealing member disposed about the valve stem.

In some embodiments, the valve assembly can be configured to be transitioned between a first configuration, a second configuration, and a third configuration. In some embodiments, in the first configuration, the gas inlet port can be placed in fluid communication with the valve inlet port such that gas can flow through a first fluid flow path in the valve assembly from the gas supply, through the valve inlet port, and out the vent. In some embodiments, in the second configuration, the gas inlet port can be placed in fluid communication with the gas outlet port such that gas can flow through a second fluid flow path in the valve assembly from the gas supply, through the valve inlet port, and out the valve outlet port, the gas flow through the second fluid flow path configured to exert a sealing force on the adjustable sealing member in the second configuration. In some embodiments, the deformable sealing member can be configured to deform in the second configuration to allow gas to flow from the gas supply, through the second fluid flow path, and to the gas outlet port. In some embodiments, the deformable sealing member can be configured to deform in response to a pneumatic pressure against at least one surface of the deformable sealing member exceeding a predetermined pneumatic pressure.

In some embodiments, the valve assembly can be configured to be transitioned to a third configuration in which the water inlet port is placed in fluid communication with the water outlet port such that water can flow from the water supply, through a third fluid flow path and out the water outlet port. In some embodiments, the valve assembly can include a deformable sealing member disposed about the valve stem.

In some embodiments, the valve assembly can include a first channel defining the valve inlet port and the valve outlet port, a second channel intersecting the first channel and defining the vent, a third channel intersecting the first channel, and a fourth channel fluidically coupled to the third channel and the adjustable sealing member. In some embodiments, the first fluid flow path can be defined when the gas inlet port is placed in fluid communication with the vent such that gas can flow into the valve assembly via the valve inlet port, through the first channel, into the second channel, and out of the valve assembly via the vent. In some embodiments, the second fluid flow path can be defined when the gas inlet port is placed in fluid communication with the gas outlet port such that gas can flow into the valve assembly via the valve inlet port, through the first channel, and out of the valve assembly via the valve outlet port. In some embodiments, gas communicated along the second fluid flow path can exert a deforming pressure on a deformable sealing member disposed about the valve stem, defining a gap between the deformable sealing member and the receptacle, such that the gas can be communicated through the gas outlet valve.

In some embodiments, the third fluid flow path can be defined when the water inlet port is placed in fluid communication with the water outlet port such that water can flow from the water supply, about the valve stem, and out of the valve assembly via the water outlet port.

In some embodiments, the apparatus further includes an actuator operably coupled to the valve assembly, the actuator configured to move the adjustable sealing member from a first position to a second position when actuated by a user to establish the third fluid flow path in the third configuration. In some embodiments, the adjustable sealing member can be configured to expand in response to at least one of pneumatic pressure, mechanical force, and hydraulic pressure. In some embodiments, the apparatus is configured to operate an endoscope to control at least one of endoscopic irrigation, insufflation, and endoscopic lens cleaning. In some embodiments, the prevention of communication of gas between the gas supply system and the water outlet port improves visualization of an operative field during use of the apparatus.

In some embodiments, the apparatus can include an endoscope handle configured to be coupled to a gas supply and a water supply, the endoscope handle defining a receptacle including a gas inlet port, a gas outlet port, a water inlet port, and a water outlet port. In some embodiments, the apparatus can further include a valve assembly configured to be disposed in the receptacle of an endoscope handle, the valve assembly including a valve stem including a valve inlet port, a valve outlet port, and a vent. In some embodiments, the apparatus can further include an adjustable sealing member disposed about the valve stem. In some embodiments, the valve assembly can be configured to be transitioned between a first configuration, a second configuration, and a third configuration. In some embodiments, in the first configuration the gas inlet port can be placed in fluid communication with the valve inlet port such that gas can flow through a first fluid flow path in the valve assembly from the gas supply, through the valve inlet port, and out the vent. In some embodiments, in the second configuration, the gas inlet port can be placed in fluid communication with the gas outlet port such that gas can flow through a second fluid flow path in the valve assembly from the gas supply, through the valve inlet port, and out the valve outlet port, the gas flow through the second fluid flow path configured to exert a sealing force on the adjustable sealing member in the second configuration.

In some embodiments, the valve assembly can be configured to be transitioned to a third configuration in which the water inlet port is placed in fluid communication with the water outlet port such that water can flow from the water supply, through a third fluid flow path and out the water outlet port.

In some embodiments, the valve assembly can include a deformable sealing member disposed about the valve stem, the deformable sealing member configured to deform in the second configuration to allow gas to flow from the gas supply, through the second fluid flow path, and to the gas outlet port. In some embodiments, the deformable sealing member can be configured to deform in response to a pneumatic pressure against at least one surface of the deformable sealing member exceeding a predetermined pneumatic pressure.

In some embodiments, the valve assembly can include a first channel defining the valve inlet port and the valve outlet port, a second channel intersecting the first channel and defining the vent, a third channel intersecting the first channel, and a fourth channel fluidically coupled to the third channel and the adjustable sealing member. In some embodiments, the first fluid flow path can be defined when the gas inlet port is placed in fluid communication with the vent such that gas can flow into the valve assembly via the valve inlet port, through the first channel, into the second channel, and out of the valve assembly via the vent. In some embodiments, the second fluid flow path can be defined when the gas inlet port is placed in fluid communication with the gas outlet port such that gas can flow into the valve assembly via the valve inlet port, through the first channel, and out of the valve assembly via the valve outlet port. In some embodiments, gas communicated along the second fluid flow path can exert a deforming pressure on a deformable sealing member disposed about the valve stem, defining a gap between the deformable sealing member and the receptacle, such that the gas can be communicated through the gas outlet valve.

In some embodiments, the third fluid flow path can be defined when the water inlet port is placed in fluid communication with the water outlet port such that water can flow from the water supply, about the valve stem, and out of the valve assembly via the water outlet port.

In some embodiments, the apparatus can further include an actuator operably coupled to the gas/water valve, the actuator configured to move the second sealing member from a first position to a second position when actuated by a user to establish the third fluid flow path in the third configuration. In some embodiments, the adjustable sealing member can be configured to expand in response to at least one of pneumatic pressure, mechanical force, and hydraulic pressure. In some embodiments, the apparatus can be an endoscope, e.g., including a handle defining the receptacle. In some embodiments, the apparatus can be configured to control endoscopic procedures such as lavage, insufflation, and visualization. In some embodiments, the prevention of communication of gas between the gas supply system and the water outlet port improves visualization of an operative field during use of the apparatus.

In some embodiments, a method for using such a valve assembly to improve visualization during endoscopic procedures can include use of such a valve assembly. In some embodiments, the valve assembly can be disposed in a receptacle of an endoscope and can include a valve inlet port, a valve outlet port, a vent, and an adjustable sealing member disposed about a valve stem. In some embodiments, the method can include conveying gas from a gas supply of the endoscope to the valve assembly during a first time period such that gas flows through the valve inlet port to the vent. In some embodiments, the method can further include obstructing the vent during a second time period such that gas conveyed from the gas supply of the endoscope to the valve assembly flows through the valve inlet port and to the adjustable sealing member to exert a sealing force against the receptacle of the endoscope. In some embodiments, the method can further include conveying gas from the gas supply of the endoscope to the valve assembly during a third time period such that gas flows from the valve inlet port through the valve outlet port and to gas outlet port of the receptacle.

In some embodiments, a deformable sealing member, disposed about the valve stem, can be dimensioned and configured to allow gas to be conveyed out of the valve assembly via the valve outlet port. In some embodiments, the method can further include aligning the deformable sealing member with the valve inlet port such that substantially no gas is communicated into the valve assembly. In some embodiments, the method can further include conveying, during a fourth time period, from a water inlet port, about the valve stem, and through the water outlet port, during a third time period, water from a water source. In some embodiments, the method can further include preventing, via the adjustable sealing member, the water from flowing into the gas outlet port. In some embodiments, obstructing the vent can cause the gas to exert a deforming force against the deforming sealing member during the second time period.

In some embodiments, the receptacle in the endoscopic device can include a gas inlet port, a gas outlet port, a water inlet port, and/or a water outlet port. In some embodiments, the valve assembly can define a first channel defining the valve inlet port and the valve outlet port, a second channel intersecting the first channel and defining the vent, a third channel intersecting the first channel, and/or a fourth channel fluidically coupled to the third channel and the adjustable sealing member.

In some embodiments, a first fluid flow path through the valve assembly can be defined when the gas inlet port is placed in fluid communication with the vent such that gas can flow into the valve assembly via the valve inlet port, through the first channel, into the second channel, and out of the valve assembly via the vent. In some embodiments, a second fluid flow path through the valve assembly can be defined when the gas inlet port is placed in fluid communication with the gas outlet port such that gas can flow into the valve assembly via the valve inlet port, through the first channel, and out of the valve assembly via the valve outlet port. In some embodiments, gas communicated along the second fluid flow path can exert a deforming pressure on a deformable sealing member disposed about the valve stem, defining a gap between the deformable sealing member and the receptacle, such that the gas can be communicated through the gas outlet valve. In some embodiments, a third fluid flow path through the valve assembly can be defined when the water inlet port is placed in fluid communication with the water outlet port such that water can flow from the water supply, about the valve stem, and out of the valve assembly via the water outlet port.

In some embodiments, the sealing force can be a first sealing force and the method can further include maintaining the first sealing force between the adjustable sealing member and the receptacle, and maintaining a second sealing force between the deformable sealing member and the receptacle, the second sealing force less than the first sealing force.

In some embodiments, the gas communicated through the gas outlet can be used for insufflation of a body cavity. In some embodiments, water communicated through the water outlet can be used for at least one of endoscopic irrigation and cleaning of an endoscopic lens. In some embodiments, the prevention of communication of gas between the gas supply system and the water outlet port improves visualization of an operative field during use of the apparatus.

FIG. 1 is a schematic illustration of an endoscopic system 100 configured to improve visualization during endoscopic procedures by capturing real-time images of the operative field of view and to relay those images back to a monitor nearby the endoscopist without blurring of the images. The endoscopic system 100 includes an endoscope handle 110 configured to be coupled to a control unit 150, and a flexible shaft 170 extending from the endoscope handle 110 and terminating in a distal end 172 that can be articulated by a user. In other words, the user can control the movement of the distal end 172 of the flexible shaft 170 along with the various functions of the endoscopic system 100 with the endoscope handle 110. The flexible shaft 170 is typically inserted into a body cavity such as the mouth, vagina, anus, urethra, or other such cavity to facilitate visualization of an internal organ or object without necessitating a surgical procedure. The distal end 172 of the flexible shaft 170 includes an optical lens (not shown) connected to a video camera (not shown) such that a real-time image of the interior space can be captured and viewed during the procedure.

The control unit 150 includes a gas supply system 152, a water supply system 154, and a vacuum source (not shown). As described herein, the gas supply system 152 is configured to deliver gas (e.g., air, $CO_2$, or another suitable gas) to the distal end 172 of the flexible shaft 170 for opening or insufflating the gastrointestinal (GI) tract. The water supply system 154 includes a sterile water reservoir 156 and a water pump 158, and is configured to supply sterile water to the distal end 172 of the flexible shaft 170 for endoscopic irrigation (i.e., lavage) and for optical lens cleaning. As described herein, the vacuum source is configured to remove bodily secretions, water from lavage, debris, excess gas, and other unwanted material from the body cavity during endoscopic procedures.

As described herein, during an endoscopic procedure, the control unit 150 is configured to deliver gas from the gas supply system 150 and water from the water supply system 152 to the distal end 172 of the flexible shaft 170, and to remove water, debris, etc. from the operative field with the vacuum source. In other words, as described above, the two primary functions that are used during an endoscopic procedure are suction and gas/water delivery, which are manually controlled by a physician using the endoscope handle 110. In some embodiments, the endoscope handle 110 includes a first valve 120 (also referred to herein as a "suction valve 120"), and a second valve 130 (also referred to herein as a "gas/water valve 130"). The suction valve 120 is primarily used to remove gas, fluid, or debris from the GI tract, however, it can also be used to facilitate the manipulation of a tissue position prior to resection or other intervention. The gas/water valve 130 is primarily used to control gas delivery from the gas supply system 150 to insufflate lumens within the GI tract and to control fluid delivery from the water supply system 152 for optical lens cleaning.

As described herein, endoscope systems are generally utilized in a similar fashion, however, the operations and internal features of the manufacturers' endoscopes can vary. In some endoscopic systems, both the suction valve 120 and the gas/water valve 130 are inserted into respective receiving receptacles (also referred to herein as "cylinders" or "receiving cylinders") in the endoscope handle 110. The receptacles are typically machined out of stainless steel, but may be made from any suitable material without limitation, and generally follow the outer contours of the specific valve with an extremely small engineering tolerance and also allow for inputs and outputs based on the respective valve functions. Specifically, as it relates to the operation of the gas/water valve 130, the receiving cylinder has two inputs (i.e., gas inlet and water inlet) and two outputs (i.e., gas outlet and water outlet). In addition, the gas/water valve 130 includes several sealing members (not shown) disposed on a valve stem (not shown) and is configured to maintain any one of three functional configurations when disposed in the receiving cylinder (i.e., open, covered, and depressed). The open, covered, and depressed configurations are herein known as a first configuration, a second configuration, and a third configuration, respectively. The valve stem has a primary radial passageway (not shown) fluidically coupled to a primary axial passageway (not shown) that is fluidically coupled to a vent (not shown). The gas for insufflation can be directed through the primary radial passageway and either vents through the primary axial passageway or continues through the primary radial passageway to exit the gas/water valve 130 by way of a gas/water outlet.

When the gas/water valve 130 is in use, the first configuration allows gas to pass from the control unit 150, through the gas inlet port and into a central location within the receiving cylinder between two seals on the valve stem, and exit the gas/water valve 130 to the atmosphere through the vent (also referred to as the release hole) in the center of the gas/water valve 130. In some embodiments, the first configuration is the baseline or default configuration because it is the configuration maintained when the user is not actively interacting with the gas/water valve 130. In other words, when the user completes a task, such as moving the distal portion of the endoscopic handle 110 into position related to an organ, and releases the operational controls, the gas/water valve 130 will return to the first configuration. The gas/water valve 130 can also be maintained in the first configuration while other functions or controls of the endoscopic system 100 are being manipulated or engaged by the user.

The user can transition the gas/water valve 130 from the first configuration to the second configuration by obstructing the vent in the center of the gas/water valve 130 such that gas cannot flow out to the atmosphere. When the vent is digitally covered by the user (e.g., an endoscopist or a physician), the receiving cylinder begins to pressurize, and a deformable sealing member (not shown) on the valve stem intentionally deforms, allowing gas to be redirected past the deformable sealing member and to exit the receiving cylinder via the gas outlet port to the distal end 172 of the flexible shaft 170. The gas/water valve 130 also includes an adjustable sealing member (not shown) configured to expand and contract (e.g., pneumatically, mechanically, hydraulically, etc.) to provide an airtight seal between the gas inlet/outlet and the water inlet/outlet. In other words, as pressure builds in the receiving cylinder, the adjustable sealing member expands in response to the increased pressure to provide an airtight and/or fluid-tight seal between the gas/water valve 130 and the receiving cylinder to prevent pressurized gas from leaking into the water inlet and/or water outlet. In some embodiments, the adjustable sealing member is both physically and fluidically coupled to the gas/water valve 130 such that as pressure builds in the system, pressure also builds within or against the adjustable sealing member, causing it to deform (e.g., expand, enlarge, inflate, grow, etc.) against the receiving cylinder and/or the gas/water valve. In other words, as potentially deforming stress from system gas pressure is exerted upon the adjustable sealing member, it expands to more effectively seal the space between the gas/water valve 130 and the receiving cylinder. In some embodiments, the receiving cylinder includes a channel (not shown) into which the adjustable sealing member is at least partially disposed and the adjustable sealing member is configured to deform in the channel.

In some embodiments, the valve stem includes a secondary axial passageway (not shown) fluidically coupled to the primary radial passageway, and the secondary axial passageway is configured to allow pressurized gas to flow to the adjustable sealing member. In some embodiments, the secondary axial passageway is fluidically coupled to a secondary radial passageway (not shown), which is substantially aligned and in fluid communication with the adjustable sealing member. In some embodiments, the secondary radial passageway is a plurality of passages distributed about the valve stem such that pressure applied to the adjustable sealing member is substantially even. In other words, in the second configuration, the gas pressure or fluid pressure that builds within the receiving cylinder between the deformable sealing member and adjustable sealing member is equal to or greater than the gas pressure within the adjustable sealing member.

In some embodiments, the adjusting force can be mechanically applied against the adjustable sealing member such that the adjusting force is sufficiently large to overcome the potentially deforming gas pressure exerted upon the adjustable sealing member from within the gas/water valve 130. In some embodiments, an actuator can be configured to apply the force and/or pressure against the adjustable sealing member.

The user can transition the gas/water valve 130 to the third configuration by depressing the gas/water valve 130. When the gas/water valve is depressed, the gas is prevented from entering the receiving cylinder and it is redirected to the water supply system 154 (i.e., the water reservoir), which begins to pressurize and force fluid (e.g., sterile water) to flow from the water supply system 154, through the endoscope umbilical to the water inlet port of the gas/water valve 130, through the receiving cylinder (e.g., about the valve stem between two seals) to the water outlet port, and to the distal end 172 of the flexible shaft 170. This flow of sterile water is directed across the lens in order to clear away debris and improve visualization.

FIGS. 2A-2C and 3-7 illustrate a gas/water valve 230, according to an embodiment. As described above with reference to the gas/water valve 130, the gas/water valve 230 is configured to prevent water flow across a lens (not shown) of an endoscopic system (not shown) during a clinical procedure, the water flow known to detrimentally obscure visualization for an endoscopist. In some embodiments, portions and/or aspects of the gas/water valve 230 are substantially similar in form and/or function to the corresponding portions and/or aspects of the gas/water valve 130 described above with reference to FIG. 1. Accordingly, such similar portions and/or aspects are not described in further detail herein.

As described herein, during an endoscopic procedure, a control unit is configured to deliver gas (e.g., air, $CO_2$, or any other suitable gas) from a gas supply system and water from a water supply system to the distal end of an endoscope, and to remove water, debris, etc. from the operative field with a vacuum source. In other words, as described above, the two primary functions that are used during an endoscopic procedure are suction and gas/water delivery, which are manually controlled by a physician using an endoscope handle. In some embodiments, the endoscope handle includes a first valve (not shown; also referred to herein as a "suction valve"), and a second valve 230 (also referred to herein as a "gas/water valve 230" and a "valve assembly 230"). The suction valve is primarily used to remove gas, fluid, or debris from the GI tract, however, it can also be used to facilitate the manipulation of a tissue position prior to resection or other intervention. The gas/water valve 230 is primarily used to control gas delivery from the gas supply system to insufflate lumens within the GI tract and also to control fluid delivery from the water supply system for optical lens cleaning.

As described herein, endoscope systems are generally utilized in a similar fashion, however, the operations and internal features of the manufacturers' endoscopes can vary. In some endoscopic systems, the gas/water valve 230 is inserted into a receiving receptacle 250 (also referred to herein as "a cylinder 250" or "a receiving cylinder 250") in the endoscope handle. The receptacle 250 is typically machined out of stainless steel, but may be made from any suitable material without limitation, and generally follows the outer contours of the gas/water valve 230 with an extremely small engineering tolerance and also allows for inputs and outputs based on the valve functions. Specifically, as it relates to the operation of the gas/water valve 230, the receiving cylinder has a gas inlet 252, and a gas outlet 254, a water inlet 256, and a water outlet 258. In addition, the gas/water valve 230 includes a first sealing member 262, a second sealing member 264, a third sealing member 266, and a fourth sealing member 268, each disposed about a valve stem 240. In some embodiments, the gas/water valve 230 defines a valve inlet port 241*a* and a valve outlet port 241*b*.

In some embodiments, one or more of the components of the device, e.g., the valve stem 240 can be monolithic (e.g., a single piece). In some embodiments, one or more of the components of the device can include a suitable material such as, for example, a thermoplastic material. Other suitable materials can include but are not limited to polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide). PEO-PPO-PEO (pluronics), rubber, plastic (e.g., polycarbonates), ABS, MABS, silicone, or the like, or combinations thereof.

Briefly, the first sealing member 262 is disposed and configured to contain gas and/or water within the gas/water valve 230. The second sealing member 264 is disposed and configured to selectively direct gas flow between the gas inlet 252 and the gas outlet 254 and can be configured to deform, e.g., at a particular pneumatic pressure. The third sealing member 266 is disposed and configured to isolate the gas flow from the water flow. The fourth sealing member 268 is disposed and configured to prevent or allow water flow for lens cleaning based upon the configuration of the gas/water valve 230.

In some embodiments, a lubricant, an antimicrobial, a solvent, or other such material can be disposed onto or incorporated into any components of the described device. In some embodiments, the lubricant can include an oil-based lubricant such as polydimethyl siloxane, trifluoropropylmethylsiloxane, polytrifluoropropylmethyl siloxane, a copolymer of dimethylsiloxane, a silicone-based lubricant, diisopropyl adipate, purcellin oil, glycerol tribehenate, silicone oil, a surfactant, sorbitan monooleate, sorbitan trioleate, or the like, or combinations thereof. In some embodiments, the antimicrobial agent (or biocidal agent) can include an antibiotic, an antiseptic, an antiviral agent, an antifungal agent, a disinfectant, or a combination thereof. In some embodiments, the antimicrobial agent can include but is not limited to phenol, quaternary ammonium, guanidine, taurolidine, parachlorometaxylenol, silver sulfadiazine, silver oxide, silver nitrate, pyridinium, benzalkonium chloride, cetrimide, benethonium chloride, cetylpyridinium chloride, dequalinium acetate, dequalinium chloride, chloroxylenol, aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymyxins, lipopeptide antibiotics, as well as pharmacologically acceptable sodium salts, pharmacologically acceptable calcium salts, pharmacologically acceptable potassium salts, lipid formulations, derivatives and/or analogs of the above, or combinations thereof. In some embodiments, the solvent can include but is not limited to an ethyl alcohol, an isopropanol, a propanol, a butanol, two or more lower alcohol components, for example a mixture of isopropyl alcohol and ethyl alcohol in a ratio of about 1:10 to about 1:1, a mixture of more than two alcohol components, or combinations thereof.

In some embodiments, the gas/water valve 230 is configured to maintain any one of three functional configurations when disposed in the receiving cylinder 250 (i.e., open, covered, and depressed). The open, covered, and depressed configurations are herein known as a first configuration, a second configuration, and a third configuration, respectively.

Figure 2A:
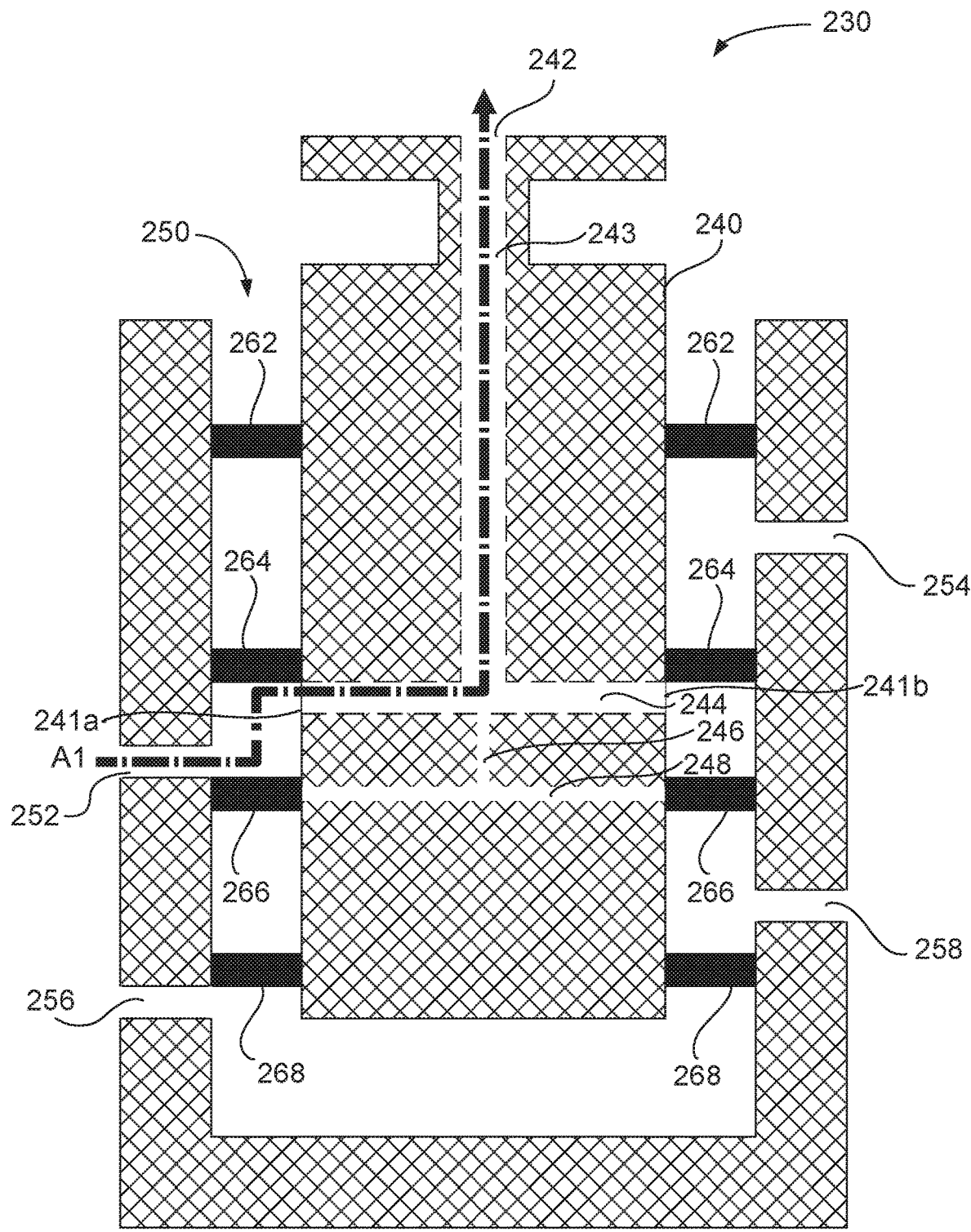
FIG. 2A is a schematic illustration of a gas/water valve in a first configuration, according to an embodiment.

As shown in FIG. 2A, the valve stem 240 has a primary radial passageway 244 fluidically coupled to a primary axial passageway 243 that is fluidically coupled to a vent 242. In some embodiments, when the gas/water valve 230 is in use, the first configuration allows gas to pass from the control unit, through the gas inlet port 252, into a central location within the receiving cylinder 250 between the second sealing member 264 and the third sealing member 266, into the primary radial passageway 244, through the primary axial passageway 243 and exits the gas/water valve 230 to the atmosphere through the vent 242 in the center of the gas/water valve 230. This gas pathway is a first gas flow pathway A1. In some embodiments, the first configuration is the baseline or default configuration because it is the configuration maintained when the user is not insufflating. In other words, when the user completes a task, such as moving the distal portion of the endoscopic handle into position related to an organ, and releases the gas/water valve 230, the gas/water valve 230 will return to the first configuration.

Figure 2B:
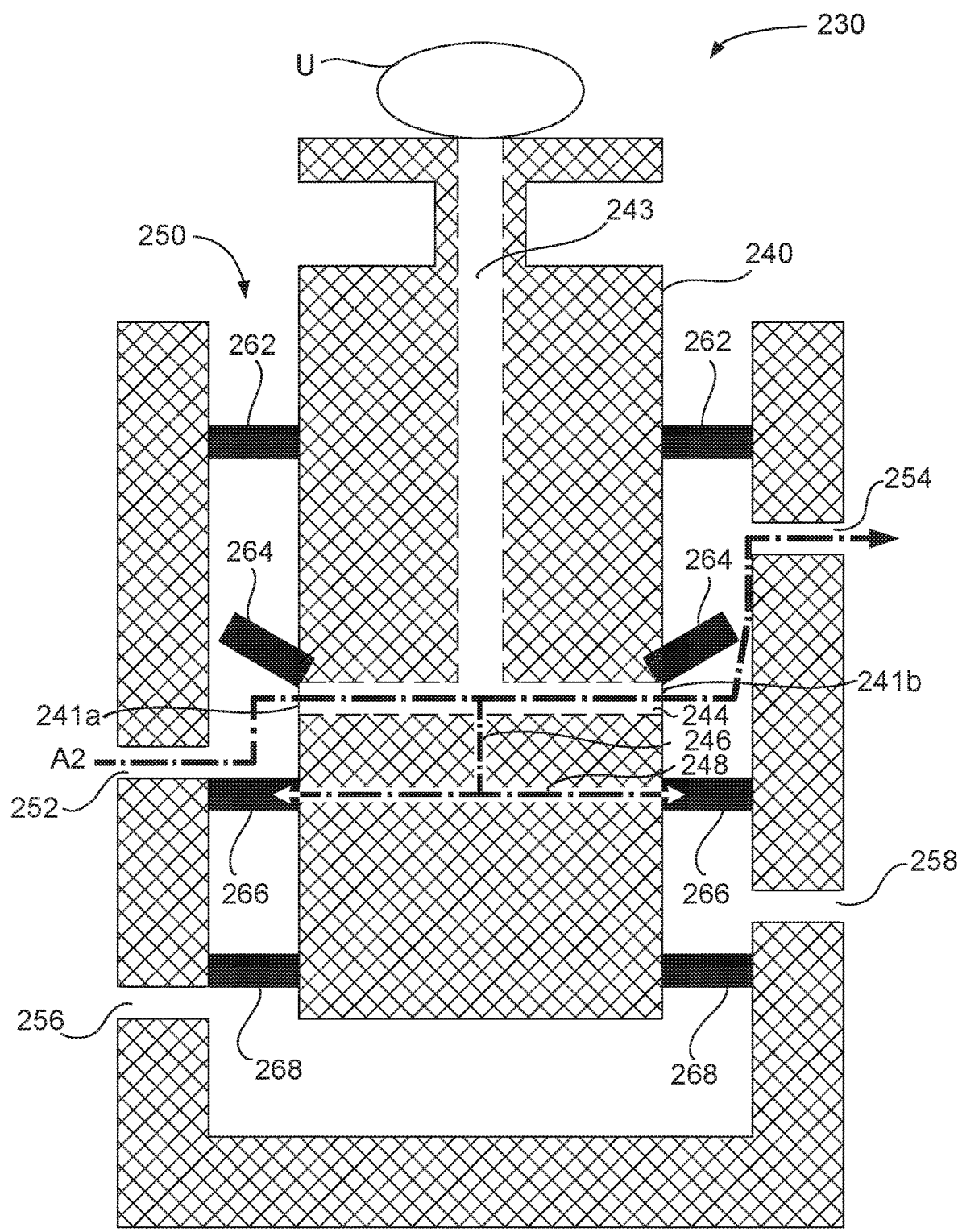
FIG. 2B is a schematic illustration of the gas/water valve of FIG. 2a in a second configuration.

The user can transition the gas/water valve 230 from the first configuration to the second configuration by obstructing the vent 242 in the center of the gas/water valve 230 such that gas cannot flow out to the atmosphere, as shown in FIG. 2B. When the vent 242 is digitally covered by a user's finger U, the space between the receiving cylinder 250 and the valve stem 240 begins to pressurize, and the deformable second sealing member 264 on the valve stem 240 intentionally deforms, allowing the gas to be redirected through the primary radial passageway 244, past the deformable second sealing member 264 and out of the receiving cylinder 250 via the gas outlet port 254 to the distal end of the flexible shaft. In other words, the gas from the gas supply system flows through the primary radial passageway 244 and either vents through the primary axial passageway 243 according to first gas flow pathway A1 in the first configuration, or continues through the primary radial passageway 244 to exit the gas/water valve 230 via the gas outlet 254, known as a second gas flow pathway A2 in the second configuration.

The gas/water valve 230 also includes the third sealing member 266, which can be an adjustable sealing member configured to expand and contract (e.g., pneumatically, mechanically, hydraulically, etc.) to provide an airtight seal between the gas inlet 252/outlet 254 and the water inlet 256/outlet 258. In other words, as pressure builds in the receiving cylinder 250, the adjustable third sealing member 266 expands in response to the increased pressure to provide a fluid-tight seal between the gas/water valve 230 and the receiving cylinder 250 to prevent pressurized gas from leaking into the water inlet 256 and/or water outlet 258. In some embodiments, the adjustable third sealing member 266 is both physically and fluidically coupled to the gas/water valve 230 such that as pressure builds in the system, gas or fluid pressure also builds within or against the adjustable third sealing member 266, causing it to deform (e.g., expand, enlarge, inflate, grow, etc.) against the receiving cylinder 250 and/or the valve stem 240 of the gas/water valve 230. In other words, as potentially deforming stress from system gas pressure is exerted upon the adjustable third sealing member 266, it expands to more effectively seal the space between the gas/water valve 230 and the receiving cylinder 250. In some embodiments, the receiving cylinder 250 includes a channel (not shown) into which the adjustable third sealing member 266 is at least partially disposed and the adjustable third sealing member 266 is configured to deform in the channel.

In some embodiments, the valve stem 240 includes a secondary axial passageway 246 fluidically coupled to the primary radial passageway 244, the secondary axial passageway 246 configured to allow pressurized gas to flow from the primary radial passageway 244 into the adjustable third sealing member 266. In some embodiments, the secondary axial passageway 246 is fluidically coupled to a secondary radial passageway 248, which is substantially aligned and in fluid communication with the adjustable third sealing member 266. In some embodiments, the secondary radial passageway 248 is a plurality of passages distributed about the valve stem 240 such that pressure applied to the adjustable third sealing member 266 is substantially even. In other words, in the second configuration, the gas pressure that builds within the receiving cylinder 250 between the deformable second sealing member 264 and adjustable third sealing member 266 is substantially equal or equal to the gas or fluid pressure within the adjustable third sealing member 266.

In some embodiments, the adjusting force can be mechanically applied against the adjustable third sealing member 266 such that the adjusting force is sufficiently large to overcome the potentially deforming gas pressure exerted upon the adjustable third sealing member 266 from within the gas/water valve 230. In some embodiments, an actuator (not shown) can be configured to apply the force and/or pressure against the adjustable sealing member.

In some embodiments, the adjustable third sealing member 266 can be made from any suitably deformable yet durable material, including but not limited to natural rubber, synthetic rubber, plastics, polyethylene, polypropylene, polystyrene, polyvinyl chloride, polymethyle methacrylate, polyamides, polycarbonates, polyesters, polyurethanes, polyvinylidene chloride, acrylonitrile butadiene styrene, polyepoxides, polytetrafluoroethylenes, phenolics, melamine formaldehyde, urea-formaldehyde, polyetheretherketone, polyetherimides, silicones, furans, polysulfones, elastomeric materials such as neoprene, isoprene, ethylene dichloride, butadiene-based synthetic rubbers, latex, 1,3-butadiene-styrene copolymers, isobutylene, polybutadiene, styrene ethylene butylene styrene copolymers, styrene block copolymers, thermoplastic polyester-esters, fluoro silicone, fluorocarbon rubber, ethylene propylene, polyisoprene, any other suitable material, and any combination thereof.

Figure 2C:
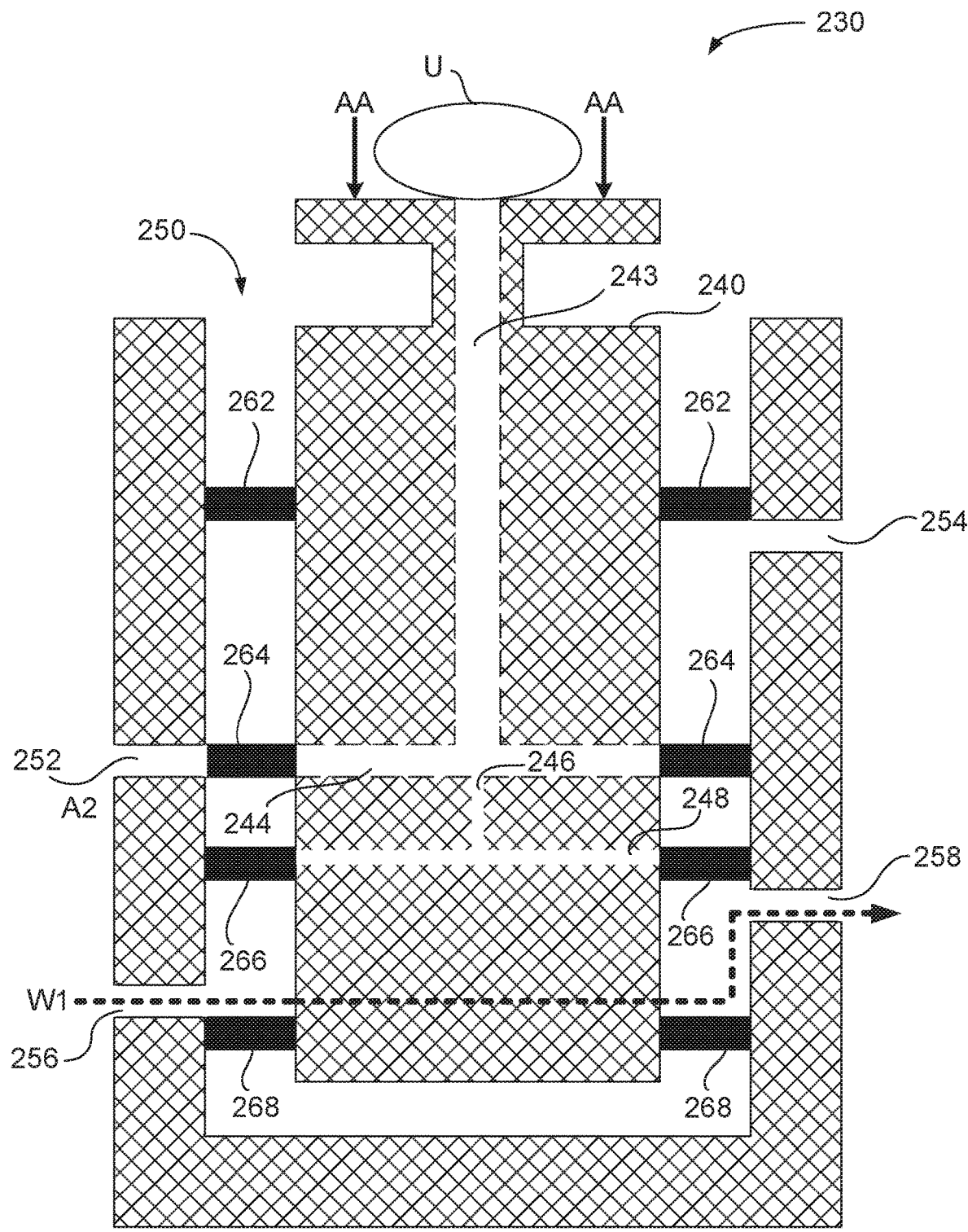
FIG. 2C is a schematic illustration of the gas/water valve of FIG. 2a in a third configuration.
Figure 3:
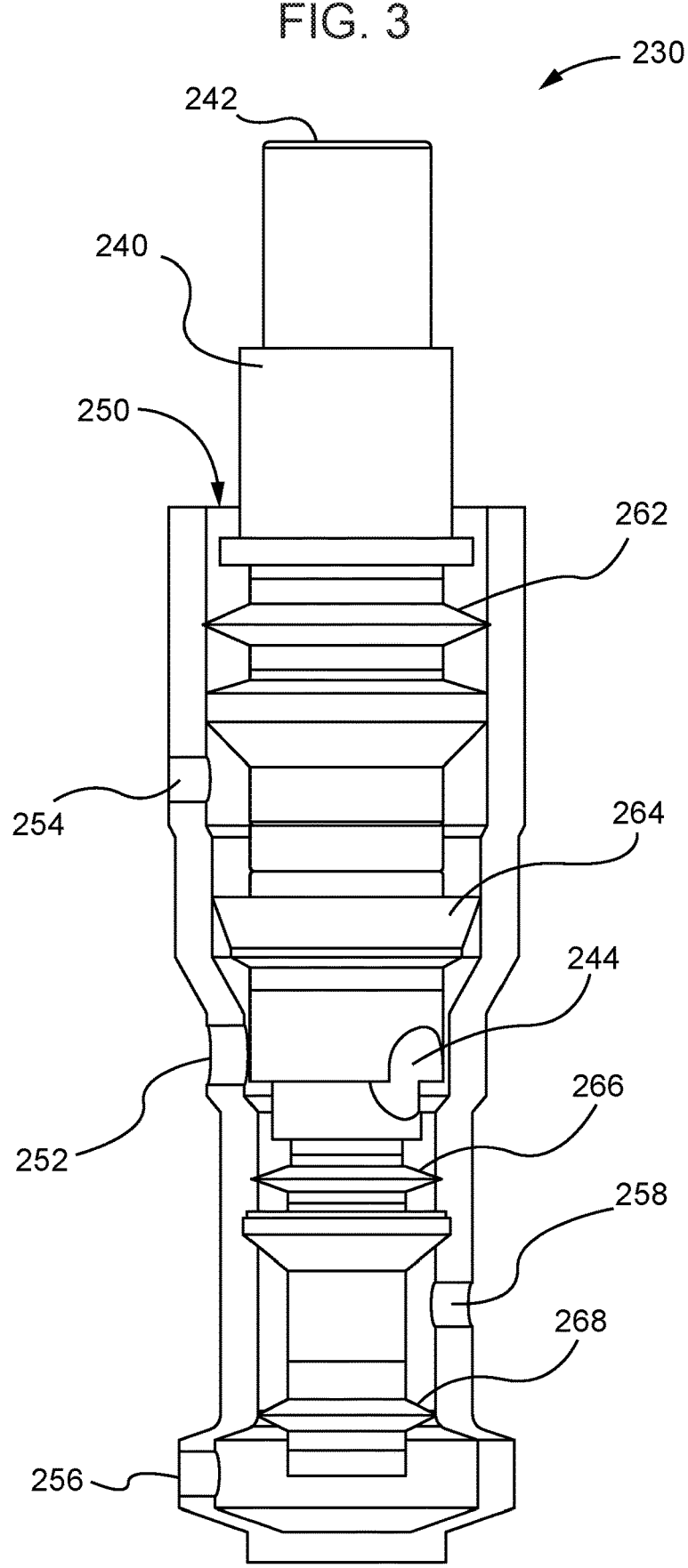
FIG. 3 is a partial cross-sectional view of a gas/water, according to an embodiment.
Figure 6:
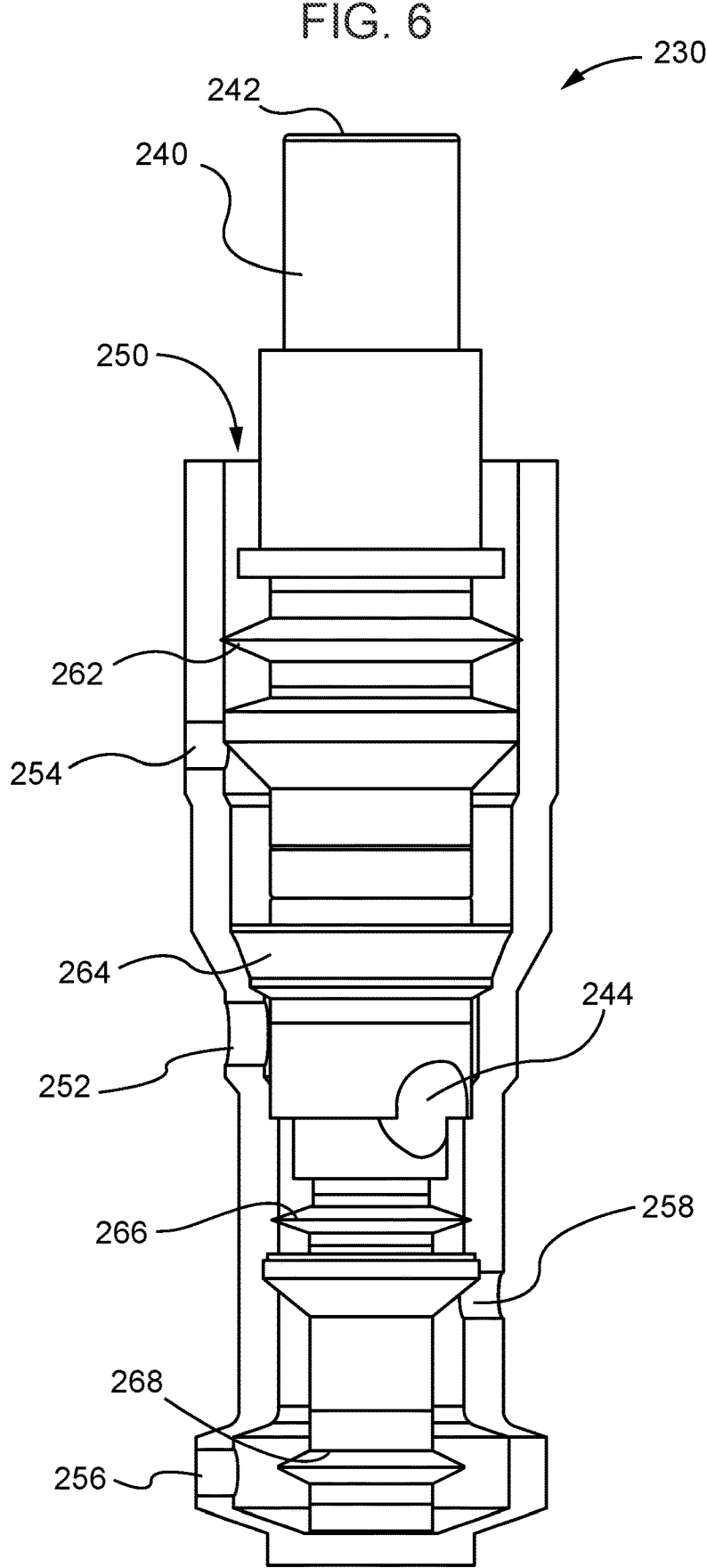
FIG. 6 is a perspective view of a gas/water valve, according to an embodiment.
Figure 7:
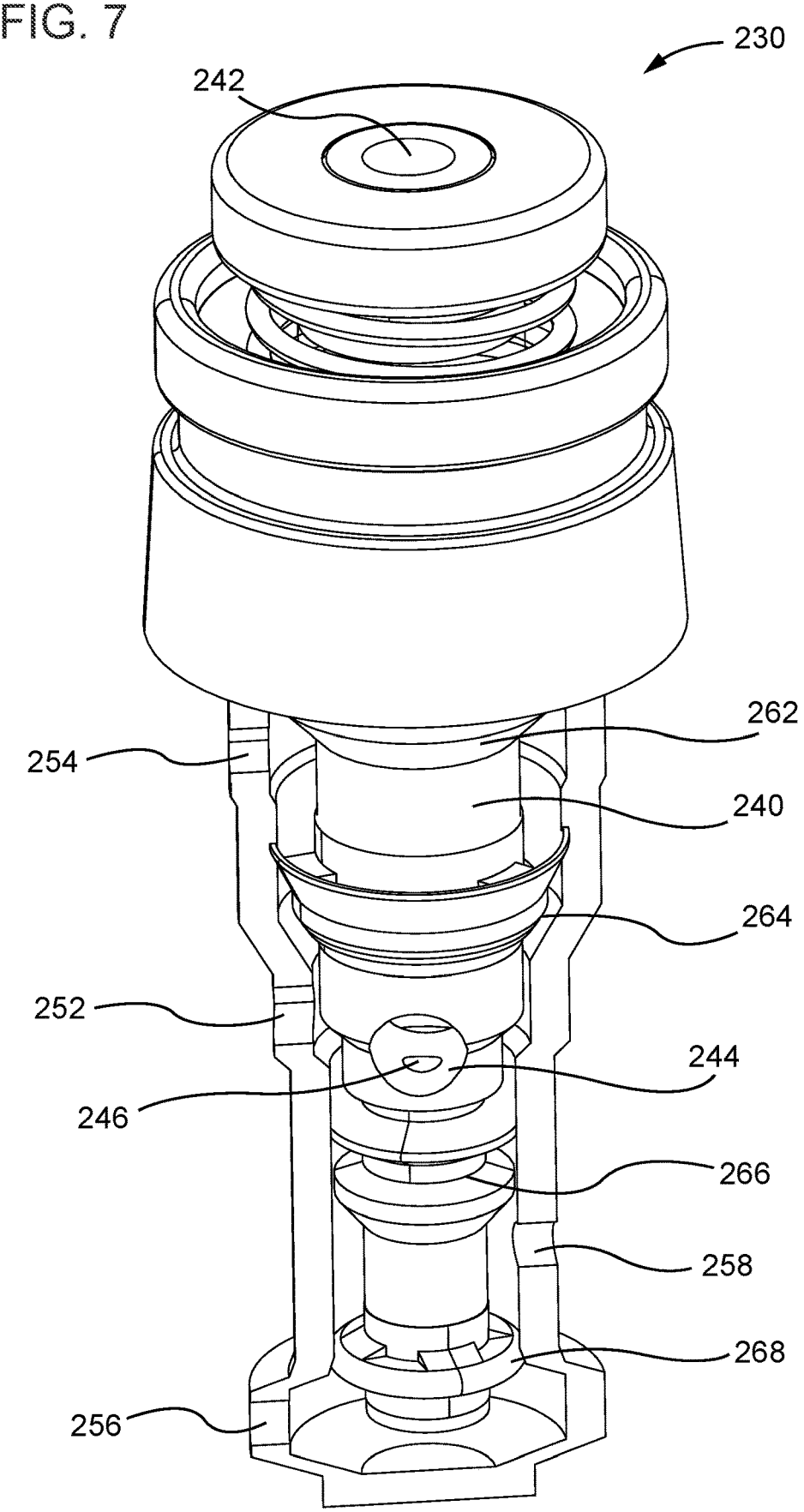
FIG. 7 is a perspective view of a gas/water valve, according to an embodiment.

The gas/water valve 230 can be transitioned to the third configuration when the gas/water valve 230 is depressed by the user's finger U, as depicted by arrows AA in FIG. 2C. When the gas/water valve 230 is depressed, the gas is prevented from entering the receiving cylinder 250 and it is redirected to the water supply system (i.e., the water reservoir), which begins to pressurize and force fluid (e.g., sterile water) to flow from the water supply system, through the endoscope umbilical to the water inlet port 256 of the gas/water valve 230, through the inner volume of the receiving cylinder 250 (e.g., about the valve stem 240 between the third sealing member 266 and fourth sealing member 268) to the water outlet port 258, and to the distal end of the flexible shaft. The water flow path is illustrated in FIG. 2C as W1.

This flow of sterile water is directed across the lens in order to clear away debris and improve visualization.

To provide an overall understanding, certain illustrative embodiments have been described; however, it will be understood by one of ordinary skill in the art that the systems, apparatuses, and methods described herein can be adapted and modified to provide systems, apparatuses, and methods for other suitable applications and that other additions and modifications can be made without departing from the scope of the systems, apparatuses, and methods described herein.

The embodiments described herein have been particularly shown and described, but it will be understood that various changes in form and details may be made. Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the scope of the disclosed and exemplary systems, apparatuses, or methods of the present disclosure.

As used herein, the term "about" and "approximately" generally mean plus or minus 10% of the value stated, for example about 250 µm would include 225 µm to 275 µm, approximately 1,000 µm would include 900 µm to 1,100 µm.

Conventional terms in the fields of endoscopic devices have been used herein. The terms are known in the art and are provided only as a non-limiting example for convenience purposes. Accordingly, the interpretation of the corresponding terms in the claims, unless stated otherwise, is not limited to any particular definition. Thus, the terms used in the claims should be given their broadest reasonable interpretation.

Although specific embodiments have been illustrated and described herein, it will be appreciated by those of ordinary skill in the art that any arrangement that is adapted to achieve the same purpose may be substituted for the specific embodiments shown. Many adaptations will be apparent to those of ordinary skill in the art. Accordingly, this application is intended to cover any adaptations or variations.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure and is submitted with the understanding that it will not be used to interpret or limit the scope or meaning of the claims.

In this Detailed Description, various features may have been grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments may be combined with each other in various combinations or permutations. The scope of the embodiments should be determined with reference to the appended claims, along with the full scope of equivalents to which such claims are entitled.

The invention claimed is:

1. An apparatus, comprising:
   a valve assembly configured to be disposed in a receptacle of an endoscope handle, the receptacle including a gas inlet port, a gas outlet port, a water inlet port, and a water outlet port, and configured to be in fluidic communication with a gas supply system and a water supply system;
   a valve stem defining a valve inlet port, a valve outlet port, a first channel fluidically coupling the valve inlet port and the valve outlet port, a vent fluidically coupled to the first channel, and a second channel parallel to the first channel and fluidically coupled to the first channel; and
   an adjustable sealing member disposed about the valve stem and fluidically coupled to the second channel via an opening of the second channel defined by an outer surface of the valve stem, at least a portion of the adjustable sealing member and the opening disposed within a plane intersecting a central axis of the valve stem,
   the valve assembly configured to be transitioned between a first configuration in which the gas inlet port is in fluid communication with the valve inlet port and the vent such that gas flows through a first fluid flow path in the valve assembly from the gas supply system, through the gas inlet port, through the valve inlet port, through a portion of the first channel, and out the vent and a second configuration in which the gas inlet port is in fluid communication with the valve inlet port and the gas outlet port such that gas flows through a second fluid flow path in the valve assembly from the gas supply system, through the valve inlet port, through the first channel, through the valve outlet port, and out the gas outlet port and such that gas flows within an interior of the valve stem from the first channel through the second channel and out the opening to exert a sealing force on the adjustable sealing member.

2. The apparatus of claim 1, wherein the valve assembly is configured to be transitioned to a third configuration in which the water inlet port is placed in fluid communication with the water outlet port such that water can flow from the water supply system, through a third fluid flow path and out the water outlet port.

3. The apparatus of claim 1, wherein the valve assembly includes a deformable sealing member disposed about the valve stem, the deformable sealing member configured to deform in the second configuration to allow gas to flow from the gas supply system, through the second fluid flow path, and to the gas outlet port.

4. The apparatus of claim 3, wherein the deformable sealing member is configured to deform in response to a pneumatic pressure against at least one surface of the deformable sealing member exceeding a predetermined pneumatic pressure.

5. The apparatus of claim 2, wherein the valve stem further defines:
a third channel intersecting the first channel and defining the vent; and
a fourth channel intersecting the first channel,
the second channel fluidically coupled to the first channel via the fourth channel.

6. The apparatus of claim 5, wherein the first fluid flow path is defined when the gas inlet port is placed in fluid communication with the vent such that gas can flow into the valve assembly via the valve inlet port, through the first channel, into the third channel, and out of the valve assembly via the vent.

7. The apparatus of claim 5, wherein the second fluid flow path is defined when the gas inlet port is placed in fluid communication with the gas outlet port such that gas can flow into the valve assembly via the valve inlet port, through the first channel, and out of the valve assembly via the valve outlet port.

8. The apparatus of claim 7, wherein gas communicated along the second fluid flow path exerts a deforming pressure on a deformable sealing member disposed about the valve stem, defining a gap between the deformable sealing member and the receptacle, such that the gas can be communicated through the gas outlet port.

9. The apparatus of claim 5, wherein the third fluid flow path is defined when the water inlet port is placed in fluid communication with the water outlet port such that water can flow from the water supply system, about the valve stem, and out of the valve assembly via the water outlet port.

10. The apparatus of claim 2, further comprising:
an actuator operably coupled to the valve assembly, the actuator configured to move the adjustable sealing member from a first position to a second position when actuated by a user to establish the third fluid flow path in the third configuration.

11. The apparatus of claim 1, wherein the adjustable sealing member is configured to expand in response to at least one of pneumatic pressure, mechanical force, and hydraulic pressure.

12. The apparatus of claim 1, wherein the endoscope handle is configured to control at least one of endoscopic irrigation, insufflation, and endoscopic lens cleaning.

13. The apparatus of claim 12, wherein the adjustable sealing member is configured to prevent communication of gas between the gas supply system and the water outlet port to improves visualization of an operative field during use of the apparatus.

14. An apparatus, comprising:
an endoscope handle configured to be coupled to a gas supply and a water supply, the endoscope handle defining a receptacle including a gas inlet port, a gas outlet port, a water inlet port, and a water outlet port;
a valve assembly configured to be disposed in the receptacle of an endoscope handle, the valve assembly including a valve stem defining a valve inlet port, a valve outlet port, a first channel fluidically coupling the valve inlet port and the valve outlet port, a vent fluidically coupled to the first channel, and a second channel parallel to the first channel and fluidically coupled to the first channel, and
an adjustable sealing member disposed about the valve stem, the adjustable sealing member extending radially outward relative to a central axis of the valve stem between at least a portion of the second channel defined within the valve stem and the receptacle,
the valve assembly configured to be transitioned between a first configuration in which the gas inlet port is in fluid communication with the valve inlet port and the vent such that gas flows through a first fluid flow path in the valve assembly from the gas supply, through the gas inlet port, through the valve inlet port, through a portion of the first channel, and out the vent and a second configuration in which the gas inlet port is in fluid communication with the valve inlet port and the gas outlet port such that gas flows through a second fluid flow path in the valve assembly from the gas supply, through the valve inlet port, through the first channel, through the valve outlet port, and out the gas outlet port and such that gas flows from the first channel through the second channel defined within the valve stem to exert a sealing force on the adjustable sealing member and radially expand the adjustable sealing member toward the receptacle.

15. The apparatus of claim 14, wherein the valve assembly is configured to be transitioned to a third configuration in which the water inlet port is placed in fluid communication with the water outlet port such that water can flow from the water supply, through a third fluid flow path and out the water outlet port.

16. The apparatus of claim 14, wherein the valve assembly includes a deformable sealing member disposed about the valve stem, the deformable sealing member configured to deform in the second configuration to allow gas to flow from the gas supply, through the second fluid flow path, and to the gas outlet port.

17. The apparatus of claim 16, wherein the deformable sealing member is configured to deform in response to a pneumatic pressure against at least one surface of the deformable sealing member exceeding a predetermined pneumatic pressure.

18. The apparatus of claim 15, wherein the valve stem further defines:

a third channel intersecting the first channel and defining the vent; and
a fourth channel intersecting the first channel,
the second channel fluidically coupled to the first channel via the fourth channel and aligned with and fluidically coupled to the adjustable sealing member.

19. The apparatus of claim 18, wherein the first fluid flow path is defined when the gas inlet port is placed in fluid communication with the vent such that gas can flow into the valve assembly via the valve inlet port, through the first channel, into the third channel, and out of the valve assembly via the vent.

20. The apparatus of claim 18, wherein the second fluid flow path is defined when the gas inlet port is placed in fluid communication with the gas outlet port such that gas can flow into the valve assembly via the valve inlet port, through the first channel, and out of the valve assembly via the valve outlet port.

21. The apparatus of claim 20, wherein gas communicated along the second fluid flow path exerts a deforming pressure on a deformable sealing member disposed about the valve stem, defining a gap between the deformable sealing member and the receptacle, such that the gas can be communicated through the gas outlet port.

22. The apparatus of claim 18, wherein the third fluid flow path is defined when the water inlet port is placed in fluid communication with the water outlet port such that water can flow from the water supply, about the valve stem, and out of the valve assembly via the water outlet port.

23. The apparatus of claim 15, further comprising:
an actuator operably coupled to the valve assembly, the actuator configured to move the adjustable sealing member from a first position to a second position when actuated by a user to establish the third fluid flow path in the third configuration.

24. The apparatus of claim 14, wherein the adjustable sealing member is configured to expand in response to at least one of pneumatic pressure, mechanical force, and hydraulic pressure.

25. The apparatus of claim 14, wherein the endoscope handle is configured to control at least one of lavage, insufflation, and visualization.

26. The apparatus of claim 25, wherein the adjustable sealing member is configured to prevent communication of gas between the gas supply and the water outlet port to improves visualization of an operative field during use of the apparatus.

27. A method for using a valve assembly to improve visualization during endoscopic procedures, the valve assembly disposed in a receptacle of an endoscope and including a valve stem and an adjustable sealing member, the valve stem defining a valve inlet port, a valve outlet port, a first channel fluidically coupling the valve inlet port and the valve outlet port, a vent fluidically coupled to the first channel, and a second channel parallel to the first channel and fluidically coupled to the first channel and defined entirely within the valve stem, the adjustable sealing member disposed about the valve stem and fluidically coupled to the second channel, the method comprising:
conveying gas from a gas supply of the endoscope to the valve assembly during a first time period such that gas flows through the valve inlet port to the vent,
obstructing the vent during a second time period such that gas conveyed from the gas supply of the endoscope to the valve assembly flows through the valve inlet port and to the adjustable sealing member via the second channel to exert an outward sealing force on the adjustable sealing member to increase a seal between the adjustable sealing member and the receptacle of the endoscope, and
conveying gas from the gas supply of the endoscope to the valve assembly during a third time period such that gas flows from the valve inlet port through the valve outlet port and to a gas outlet port of the receptacle.

28. The method of claim 27, wherein a deformable sealing member, disposed about the valve stem, is configured to allow gas to be conveyed out of the valve assembly via the valve outlet port.

29. The method of claim 28, further comprising:
aligning the deformable sealing member with the valve inlet port such that substantially no gas is communicated into the valve assembly;
conveying, during a fourth time period, from a water inlet port, about the valve stem, and through a water outlet port, during a third time period, water from a water source; and
preventing, via the adjustable sealing member, the water from flowing into the gas outlet port.

30. The method of claim 28, wherein obstructing the vent causes the gas to exert a deforming force against the deformable sealing member during the second time period.

31. The method of claim 27, wherein the receptacle includes
a gas inlet port;
a water inlet port; and
a water outlet port.

32. The method of claim 31, wherein the valve stem defines:
a third channel intersecting the first channel and defining the vent; and
a fourth channel intersecting the first channel,
the second channel fluidically coupled to the first channel via the fourth channel and aligned with the adjustable sealing member.

33. The method of claim 32, wherein a first fluid flow path through the valve assembly is defined when the gas inlet port is placed in fluid communication with the vent such that gas can flow into the valve assembly via the valve inlet port, through the first channel, into the third channel, and out of the valve assembly via the vent.

34. The method of claim 32, wherein a second fluid flow path through the valve assembly is defined when the gas inlet port is placed in fluid communication with the gas outlet port such that gas can flow into the valve assembly via the valve inlet port, through the first channel, and out of the valve assembly via the valve outlet port.

35. The method of claim 34, wherein gas communicated along the second fluid flow path exerts a deforming pressure on a deformable sealing member disposed about the valve stem, defining a gap between the deformable sealing member and the receptacle, such that the gas can be communicated through the gas outlet port.

36. The method of claim 31, wherein a third fluid flow path through the valve assembly is defined when the water inlet port is placed in fluid communication with the water outlet port such that water can flow from a water source, about the valve stem, and out of the valve assembly via the water outlet port.

37. The method of claim 27, wherein the outward sealing force is a first sealing force, the method further comprising:
maintaining the first sealing force between the adjustable sealing member and the receptacle; and maintaining a second sealing force between a deformable sealing member and the receptacle, the second sealing force less than the first sealing force.

38. The method of claim 27, wherein the gas communicated through the gas outlet port is for insufflation of a body cavity.

39. The method of claim 29, wherein the water communicated through the water outlet port is for at least one of endoscopic irrigation and cleaning of an endoscopic lens.

* * * * *